United States Patent [19]

Busta et al.

[11] 4,018,650

[45] Apr. 19, 1977

[54] METHOD OF PRODUCTION AND RECOVERY OF PROTEIN FROM FOOD WASTES

[75] Inventors: Francis F. Busta, St. Paul; Bruce E. Schmidt, Golden Valley; Larry L. McKay, St. Paul, all of Minn.

[73] Assignee: The Regents of the University of Minnesota, Minneapolis, Minn.

[22] Filed: Oct. 1, 1975

[21] Appl. No.: 618,289

[52] U.S. Cl. .............................. 195/28 R; 195/111; 210/11; 426/13; 426/53; 426/55

[51] Int. Cl.² .......................................... C12B 1/00

[58] Field of Search ........... 426/13, 53, 55; 210/11; 195/28 R, 111

[56] References Cited

UNITED STATES PATENTS 3,711,392  1/1973  Metzger .............................. 195/111

*Primary Examiner*—Raymond N. Jones
*Assistant Examiner*—Robert J. Warden
*Attorney, Agent, or Firm*—Burd, Braddock & Bartz

[57] ABSTRACT

A method of production and recovery of protein from food wastes according to which a medium composed of various combined food wastes and containing both a protein source (such as collagen) and a carbohydrate source (such as starch) is modified by the action of selected microbial species (such as *Bacillus subtilis*). The resulting Bacillus-modified enriched liquid medium permits the growth of more fastidious organisms (such as *Lactobacillus acidophilus*) that are acceptable as a single cell protein source. As an alternative and prior to the introduction of the *Lactobacillus*, the modified medium may be fortified by the addition of other food wastes, (such as cheese whey or spent brewer's yeast cells). The final recovery of protein from the fastidious organisms may be accomplished by any one of the established methods of protein or food recovery and/or isolation.

13 Claims, 6 Drawing Figures

METHOD OF PRODUCTION AND RECOVERY OF PROTEIN FROM FOOD WASTES

BACKGROUND OF THE INVENTION

1. Field of the Invention

This invention relates to a method of recovery of single cell protein (SCP) from food wastes. More particularly, this invention relates to a method of recovery of protein from food wastes in which a medium composed of various combined food wastes and containing both a protein source and a carbohydrate source is modified by the action of selected microbial species. The resulting modified liquid medium permits the growth of more fastidious organisms that are acceptable as a single cell protein source. The final recovery of protein from the fastidious organisms may be accomplished by any one of the established methods of protein or food recovery and/or isolation. Single cell protein is used as a protein additive or supplement for food for human use and as an animal feed and feed supplement.

2. Description of the Prior Art

The only materials produced industrially as single cell protein (SCP), at present available to the commercial animal feed industry, are those derived from hydrocarbon grown yeasts. While these processes produce SCP of demonstrably high quality, the methanol and the various hydrocarbons used in these processes are not waste materials. In fact, they are very useful products having high priority utility in energy production and other industrial fields.

In a recent paper (Bough et al, 1972, App. Microbiol. 24:2: 226–235), there is described a means of producing single cell protein from collagenous by-products of the meat industry through the continuous cultivation of *Bacillus megaterium*. The protein obtained from the *B. megaterium* cells was found to be superior to the collagen from a nutritional standpoint. An improved amino acid balance and higher protein efficiency ratio were evidence of this. This is a one step process using only one organism to ferment only one substrate.

Many of the processes for the utilization of complex carbohydrates such as starch or cellulose involve the use of two or more fermenting organisms. The first fermentation breaks down the complex carbohydrate into simpler sugars which can be used in the secondary fermentation for the production of single cell protein. The proposed process belongs to this general area of single cell protein manufacture.

One such process is the symba yeast process described by Lars Emmelin (Emmelin, L. 1974. Environmental Planning in Sweden N. 52. Protein from Waste Water. Current Sweden 52). Starch containing waste water from potato processing plants is fermented by a mixed culture containing a fungus, *Endomycopsis fibuliger* and a *Candida* yeast. The fungus produces amylases which hydrolyze the starch giving simpler sugars which can be fermented by the yeast. The yeast, which is the only product of the system, is considered a good source of protein.

Another process which depends on the action of fungal enzymes to hydrolyze complex carbohydrate molecules is the "koji fermentation," described in two papers by Professor Wm. Stanton (Stanton, W. R. et al, 1969. Process Biochem. 5:4:45–51 and Stanton, W. R. 1972. Process Biochem. 7:2.) It has been adapted by others (Kassai, P. T. et al, 1973. Adaptation of the "koji fermentation" to Waste Disposal. Abstracts of the Annual Meeting of the ASM. 73,3. and Savage, J. et al. 1973. Growth of *Candida utilis* on Chemical, Microbial and Enzymatic Hydrolysates of Swine Waste. Abstracts of the Annual Meeting of the ASM. 73.). This fermentation consists of an aerobic enzyme producing stage (koji) followed by an anaerobic aqueous phase (moromi) in which the enzymes catalyze degradation of the complex molecules found in the original waste materials. While this process is normally applied to the fermentation of rice and other starchy materials in the Orient for the production of fermented food products, both of these groups adapted the process to the degradation of animal fecal wastes for the production of single cell protein.

SUMMARY OF THE INVENTION

The present invention is directed to the two stage production of single cell protein for use as an animal feed and food supplement. A medium containing both a protein source and a carbohydrate source from combined readily available food wastes is modified in a first stage by microbial action. The resulting modified medium permits the growth in a second stage of more fastidious organisms which are acceptable as a single cell protein source. Potential sources for the protein material include packing house wastes. Potential sources for the carbohydrate material include wastes from potato processing plants, grain milling wastes, and the like.

The method comprises generally the following steps: First, preparing a liquid medium from the combined food wastes, inoculating that medium with a species of Bacillus, such as *Bacillus subtilis*, maintaining the medium under conditions favorable to microbial growth to produce the modified medium, then inoculating that modified medium with another organism, a species of Lactobacillus, such as *L. acidophilus*, maintaining this medium under conditions favorable to growth of the second organism, and finally, recovering the resulting protein.

As a modification, the modified medium may be fortified by the addition of other food wastes such as whey produced as a by-product of cheese making or spent brewer's yeast cells, or the like.

The process according to the present invention has the advantage of allowing the degradation of starchy materials and other complex carbohydrates with the simultaneous production of a useful food product of some of the prior art processes and, in addition, has the following advantages:

1. The mixture of waste materials eliminates the need for the expensive addition of a nitrogen source or other growth factor. All of the needs for good growth of the fermenting organisms are supplied by the waste material.

2. The combination of carbohydrate and protein containing wastes allows the fast growth of an organism which is both proteolytic and amylytic. The resulting medium can be used for the growth of a more fastidious organism requiring simpler sugars for its growth.

3. The gram positive bacilli used in the first step are easily lysed by lysozyme. Through the use of existing technology, one can easily lyse the cells and subsequently recover the protein from the medium through heat precipitation or some other acceptable protein recovery method.

4. The second fermenting organism is more easily accepted from an aesthetic point of view because of its common use in food fermentations.

5. The process allows for the elimination of two important food wastes simultaneously. Collagenous wastes from the meat industry and starch waste from the potato industry are readily available in many agricultural areas (such as Minneapolis-St. Paul, Minn.) and are the most abundant wastes from these operations.

6. A potential for obtaining lactic acid as a product of the second fermentation gives an added economic advantage to the process.

7. The broad optima indicated for collagen and starch concentration relative to both Bacillus and Lactobacillus growth facilitates their use as fermentation substrates in light of the variability of the raw materials.

BRIEF DESCRIPTION OF THE DRAWINGS

The invention is further illustrated in the accompanying drawings in which.

DESCRIPTION OF THE PREFERRED EMBODIMENT

Figure 1:
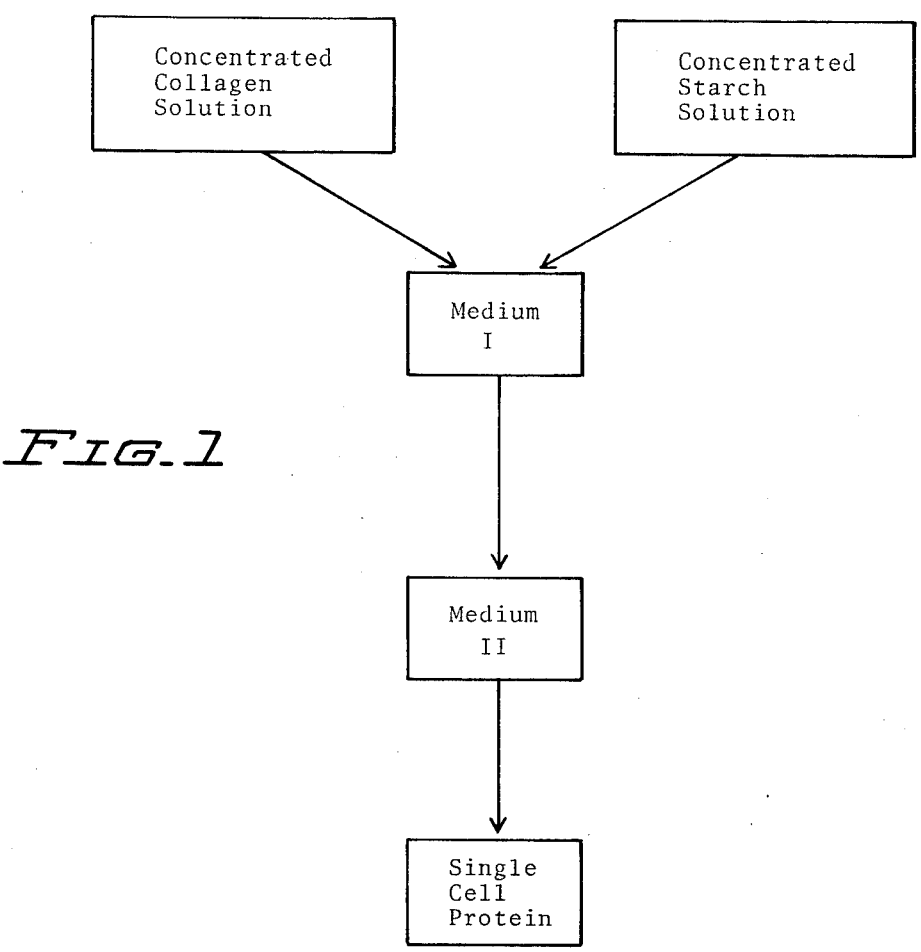
FIG. 1 is a simplified flow diagram of the process.

1. Solutions of collagen and starch are prepared to give a growth medium. The concentrations for this medium should be between about 5 to 200 and preferably 20 to 100 g/l collagen to about 1 to 20 g/l starch. The food wastes are cooked at a relatively high temperature equivalent to at least 121° C for 10 minutes to 150° C for 1 second to solubilize the starch and collagen and sterilize the medium. This is clarified as by filtration or continuous centrifuging. Fat is separated along with a sludge usable as animal feed.

2. A species of Bacillus, usually Bacillus subtilis or Bacillus megaterium (or Bacillus natto or Bacillus polymyxa), in amount between about 0.1 to 10% and preferably about 1%, is inoculated into this medium and grown at temperatures between about 20° and 70° C for about 1 to 36 hours (4 to 36 hours for batch processing). The optimum temperature range is between about 30° to 55° C and the preferred growth period is about 18 to 36 hours for batch processing. Other thermophilic, psycrotrophic, proteolytic, or amylitic Bacillus species useful in carrying out the process include the following:

| | |
|---|---|
| B. licheniformis | B. epiphytus |
| B. cereus | B. psychrosaccharolyticus |
| B. megaterium | B. macquariensis |
| B. polymyxa | B. laevolacticus |
| B. macerans | B. racemilacticus |
| B. circulans | B. filicolonicus |
| B. stearothermophilus | B. thiaminolyticus |
| B. coagulans | B. ciroflagellosus |

-continued

| | |
|---|---|
| B. firmus | B. alealophilus |
| B. amyloliquefacians | B. aminovorans |
| B. medusa | B. globisporus |
| B. maroccanus | B. psychrophilus |
| B. pacificus | B. acidocaldarius |
| B. lentus | |

3. The cells may optionally be lysed either by the addition of lysozyme or the use of immobilized lysozyme. After lysis the medium is incubated at temperatures between about 20° and 70° C to increase the concentration of reducing sugars and hydrolyze more starch. While there is starch left in the medium, a longer incubation period will give a greater yield of reducing sugars and better growth of Lactobacillus sp. in the second fermentation step. The cells of Bacillus sp. need not by lyzed in the medium. Any other method of harvesting the cells and extracting their protein may be employed. If combined with a long growth period of Bacillus sp., the harvesting method used will not affect the breakdown of starch.

4. Cheese whey or some other reducing sugar containing material may optionally be added as a fortifying material. A relatively small amount of cheese whey (about 3.5 g/l or less) has been found to be optimal. While not essential, the addition of dried brewer's yeast cells is somewhat stimulatory.

5. The medium may be heat sterilized, especially where Bacillus sp. cells have been lysed in the medium. This serves to precipitate the protein and inactivate certain enzymes of Bacillus sp. which may be inhibitory to the growth of Lactobacillus sp.

6. A species of Lactobacillus, such as L. acidophilus, is inoculated into the medium and grown under anaerobic conditions at temperatures between about 20° and 70° C for about 1 to 36 hours (4 to 36 hours for batch processing). The optimum temperature for the growth of most Lactobacillus sp. is about 30° to 55° C for about 18 to 24 hours in batch processing. The pH is controlled at as low a value as possible (between about pH 3.5 and 6.5) which will still permit good growth of Lactobacillus sp. Since Lactobacilli grow at a lower pH than most organisms, this inhibits the growth of most contaminating organisms. Other Lactobacillus species useful in carrying out the process include the following:

| | |
|---|---|
| L. leichmannii | L. xylosus |
| L. jensenii | L. plantarum |
| L. lactis | L. fermentum |
| L. helviticus | L. brevis |
| L. casei subsp. pseudoplantarum | L. buchneri |

7. The cells of Lactobacillus sp. are harvested and protein is extracted. In general the steps in protein extraction and purification are the following: (a) degradation of the cell walls by mechanical, physical, enzymatic, or chemical methods; (b) precipitation of the protein heat or chemically; (c) separation of the nucleic acids by chemical or enzymatic methods; (d) further purification of the protein; and (e) formation of useful protein product by many accepted and proven methods. Many proposals have been put forth for accomplishing each of these steps. Reference is made, for example, to Biotechnology and Bioengineering, Vol. XI, pp 37–51; Vol. XII, pp 947–59; Vol. XIII, pp

EXAMPLES

Based on the model process (FIG. 1), a response surface experiment consisting of 30 trials was devised. For laboratory use, solutions of collagen and starch simulating actual food wastes were prepared. The five variables: collagen and starch concentration in medium I, length of time of *Bacillus subtilis* growth, and levels of fortification by cheese whey and spent yeast cells were considered. The three variables: *B. subtilis* growth, reducing sugar production from starch by *B. subtilis* amylase and *Lactobacillus acidophilus* growth were measured. Thirty-three response surfaces were generated by a computer analysis of the experimental data (Tables 1 and 2).

On the basis of these surfaces, three of the original variables were fixed. *B. subtilis* growth was found to have a slight negative effect on subsequent *L. acidophilis* growth in fortified media. Spent yeast cells and cottage cheese whey were shown to be unnecessary for the growth of *L. acidophilus*. Follow-up experiments (Tables 3 and 4) showed that a low level of cottage cheese whey, below levels measured by the response surface experiment, was necessary for the growth of *L. acidophilus*. Spent yeast cells were found to have a beneficial but non-essential effect.

TABLE 1

Growth and reducing sugar production by *Bacillus subtilis* in media composed of collagen and starch

| Trial No. | Composition of media Collagen (g/l) | Starch (g/l) | Growth Period (hrs) | Final pH | Final O.D. | Reducing sugar as maltose mg/ml |
|---|---|---|---|---|---|---|
| 1 | 4.0 | 1.0 | 4.0 | 7.0 | 0.12 | 0.08 |
| 2 | 16.0 | 1.0 | 4.0 | 6.8 | 0.20 | 0.32 |
| 3 | 4.0 | 2.0 | 4.0 | 6.7 | 0.09 | 0.10 |
| 4 | 16.0 | 2.0 | 4.0 | 6.9 | 0.17 | 0.37 |
| 5 | 4.0 | 1.0 | 16.0 | 6.7 | 1.47 | 0.26 |
| 6 | 16.0 | 1.0 | 16.0 | 7.4 | 1.20 | 0.49 |
| 7 | 4.0 | 2.0 | 16.0 | 6.7 | 0.46 | 0.50 |
| 8 | 16.0 | 2.0 | 16.0 | 7.6 | 2.25 | 0.64 |
| 9 | 4.0 | 1.0 | 4.0 | 7.0 | 0.12 | 0.09 |
| 10 | 16.0 | 1.0 | 4.0 | 6.8 | 0.20 | 0.33 |
| 11 | 4.0 | 2.0 | 4.0 | 6.7 | — | 0.09 |
| 12 | 16.0 | 2.0 | 4.0 | 6.9 | 0.17 | 0.37 |
| 13 | 4.0 | 1.0 | 16.0 | 6.7 | 1.47 | 0.26 |
| 14 | 16.0 | 1.0 | 16.0 | 7.7 | 2.0 | 0.56 |
| 15 | 4.0 | 2.0 | 16.0 | 6.7 | 0.46 | 0.46 |
| 16 | 16.0 | 2.0 | 16.0 | 7.6 | 2.25 | 0.65 |
| 17 | 0.718 | 1.5 | 10.0 | 7.1 | — | <0.03 |
| 18 | 19.282 | 1.5 | 10.0 | 7.1 | 2.40 | 0.78 |
| 19 | 10.0 | 0.7265 | 10.0 | 7.1 | 0.42 | 0.24 |
| 20 | 10.0 | 2.2735 | 10.0 | 7.1 | 0.83 | 0.63 |
| 21 | 10.0 | 1.5 | 0.718 | 7.0 | — | 0.14 |
| 22 | 10.0 | 1.5 | 19.282 | 7.7 | 2.5 | 0.43 |
| 23 | 10.0 | 1.5 | 10.0 | 6.9 | 1.0 | 0.39 |
| 24 | 10.0 | 1.5 | 10.0 | 7.0 | 0.78 | 0.42 |
| 25 | 10.0 | 1.5 | 10.0 | 7.0 | 0.78 | 0.45 |
| 26 | 10.0 | 1.5 | 10.0 | 6.9 | 0.83 | 0.47 |
| 27 | 10.0 | 1.5 | 10.0 | 6.9 | 0.83 | 0.51 |
| 28 | 10.0 | 1.5 | 10.0 | 7.0 | 0.50 | 0.42 |
| 29 | 10.0 | 1.5 | 10.0 | 7.0 | 0.78 | 0.42 |
| 30 | 10.0 | 1.5 | 10.0 | 7.0 | 0.78 | 0.46 |

TABLE 2

*Lactobacillus acidophilus* growth in media modified by *Bacillus subtilis* growth and cheese whey and yeast addition

| Trial No. | Cheese whey gm/l | Yeast gm/l | pH 4 hr | 12 hr | 24 hr | O.D. 4 hr | 12 Hr | 24 hr |
|---|---|---|---|---|---|---|---|---|
| 1 | 3.44 | 1.72 | 5.4 | 4.7 | 4.6 | 0.0 | 0.07 | 0.14 |
| 2 | 3.44 | 8.0 | 5.7 | 4.6 | 4.3 | 0.07 | 0.35 | 0.47 |
| 3 | 3.44 | 8.0 | 5.6 | 5.0 | 4.3 | 0.04 | 0.10 | 0.18 |
| 4 | 3.44 | 1.72 | 5.2 | 4.3 | 4.2 | 0.03 | 0.66 | 0.70 |
| 5 | 3.44 | 8.0 | 5.8 | 4.5 | 4.0 | 0.06 | 0.18 | 0.22 |
| 6 | 3.44 | 1.72 | 7.2 | 5.1 | 4.4 | 0.04 | 0.37 | 0.52 |
| 7 | 3.44 | 1.72 | 4.7 | 4.5 | 4.5 | 0.02 | 0.11 | 0.07 |
| 8 | 3.44 | 8.0 | 7.4 | 4.9 | 4.6 | 0.03 | 0.50 | 0.52 |
| 9 | 16.0 | 8.0 | 4.7 | 4.3 | 4.2 | 0.01 | 0.13 | 0.14 |
| 10 | 16.0 | 1.72 | 5.2 | 4.8 | 4.1 | 0.23 | 0.35 | 0.61 |
| 11 | 16.0 | 1.72 | 4.5 | 4.3 | 4.4 | 0.02 | 0.11 | 0.22 |
| 12 | 16.0 | 8.0 | 6.2 | 4.2 | 4.2 | 0.05 | 0.50 | 0.54 |
| 13 | 16.0 | 1.72 | 4.7 | 4.5 | 4.3 | 0.09 | 0.13 | 0.13 |
| 14 | 16.0 | 8.0 | 5.8 | 4.7 | 4.1 | 0.02 | 0.28 | 0.43 |
| 15 | 16.0 | 8.0 | 4.8 | 4.7 | 4.7 | — | 0.07 | 0.07 |
| 16 | 16.0 | 1.72 | 6.3 | 5.3 | 4.1 | — | 0.14 | 0.68 |
| 17 | 9.72 | 4.86 | 5.2 | 4.8 | 4.1 | — | 0.04 | 0.14 |
| 18 | 9.72 | 4.86 | 5.8 | 4.5 | 4.2 | — | 0.45 | 0.52 |
| 19 | 9.72 | 4.86 | 5.7 | 5.0 | 4.5 | 0.06 | 0.15 | 0.29 |
| 20 | 9.72 | 4.86 | 5.2 | 4.8 | 4.8 | 0.01 | 0.10 | 0.13 |
| 21 | 9.72 | 4.86 | 4.8 | 4.6 | 4.3 | 0.04 | 0.16 | 0.32 |
| 22 | 9.72 | 4.86 | 8.2 | 8.1 | 7.5 | 0.02 | 0.01 | 0.10 |

TABLE 2-continued

Lactobacillus acidophilus growth in media modified by
Bacillus subtilis growth and cheese whey and yeast addition

| Trial No. | Cheese whey gm/l | Yeast gm/l | pH 4 hr | pH 12 hr | pH 24 hr | O.D. 4 hr | O.D. 12 Hr | O.D. 24 hr |
|---|---|---|---|---|---|---|---|---|
| 23 | 0.0 | 4.86 | 7.0 | 6.8 | 6.7 | 0.03 | 0.05 | 0.08 |
| 24 | 19.44 | 4.86 | 5.0 | 4.8 | 4.3 | 0.02 | 0.09 | 0.15 |
| 25 | 9.72 | 0.0 | 5.5 | 5.3 | 5.2 | 0.0 | 0.05 | 0.06 |
| 26 | 9.72 | 9.72 | 5.4 | 4.6 | 4.2 | 0.07 | 0.23 | 0.32 |
| 27 | 9.72 | 4.86 | 5.4 | 4.9 | 4.9 | 0.01 | 0.08 | 0.12 |
| 28 | 9.72 | 4.86 | 5.6 | 5.0 | 4.4 | 0.04 | 0.18 | 0.27 |
| 29 | 9.72 | 4.86 | 5.4 | 4.9 | 4.6 | 0.04 | 0.15 | 0.17 |
| 30 | 9.72 | 4.86 | 5.4 | 5.0 | 4.4 | 0.03 | 0.13 | 0.22 |

Since optimum collagen and starch concentrations had not been defined for the three responses in the first experiment, a second response surface experiment of 11 trials was undertaken. In this experiment the effects of two variables, collagen concentration and starch concentration, were measured. The growth time of B. subtilis was held constant at 4 hours. Cheese whey concentration was held constant at 3.44 g/l. Fortification with spent brewer's yeast cells was not considered. Four response surfaces (FIG. 2-5) were generated by a computer analysis of the data obtained in this experiment (Table 5).

Figure 2:
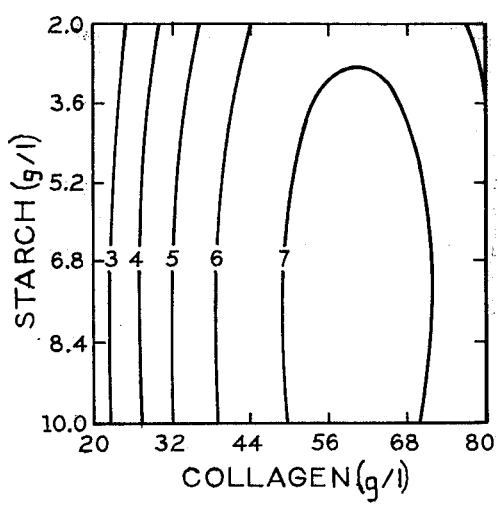
FIG. 2 is a response surface generated by computer analysis of experimental data and showing Bacillus subtilis growth.

The single most important factor affecting all of the responses appeared to be collagen concentration. A concentration of 50 g/l was the lower limit for optimal B. subtilis growth (FIG. 2). No upper limit was defined. Starch concentration had very little effect on B. subtilis growth.

Figure 3:
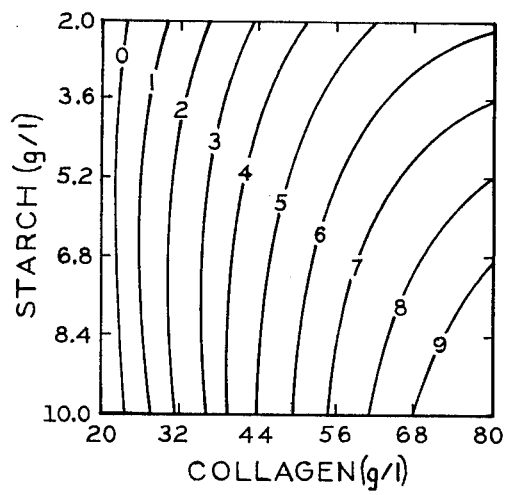
FIG. 3 is a response surface showing reducing sugar accumulation during B. subtilis growth.
Figure 4:
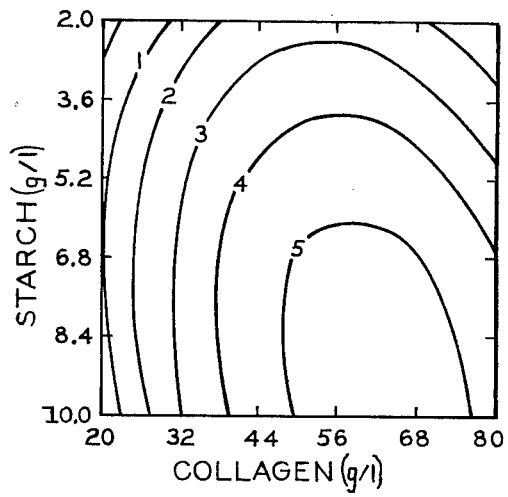
FIG. 4 is a response surface showing Lactobacillus acidophilus growth in unfortified media.
Figure 5:
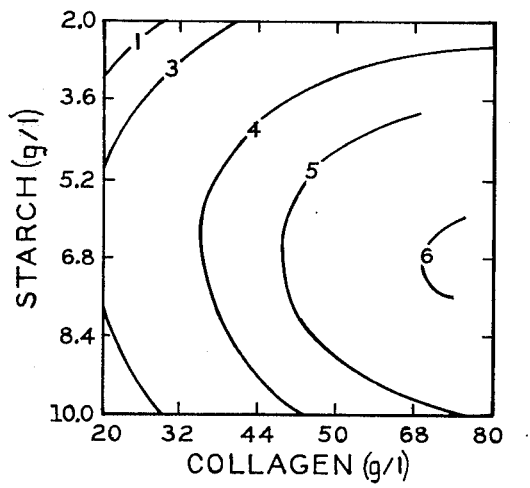
FIG. 5 is a response surface showing L. acidophilus growth in media fortified with cottage cheese whey.

Optimal conditions were not defined for reducing sugar production (FIG. 3). Increasing collagen and increasing starch both had a positive effect on reducing sugar production. The importance of reducing sugar concentration for L. acidophilus growth has been shown (Table 6). The positive effect of collagen on this response probably reflects the effect of increased B. subtilis growth.

Interpretations of the surfaces for L. acidophilus growth are more difficult. The low amount of growth obtained in unfortified media make the validity of any conclusions concerning this response (FIG. 4) questionable. However, the levels indicated by the surface appear to be reasonable. The surface for L. acidophilus growth in fortified media (FIG. 5) is somewhat weak statistically. However, the indication of high collagen levels being necessary for growth can be accepted with caution after a comparison with experimental data.

TABLE 3

Growth of L. acidophilus in a medium composed of collagen (16 g/l) and starch (2 g/l) which has been modified by B. subtilis growth and the addition of yeast and cheese whey

|  |  | 4 hr | 12 hr. | 24 hr |
|---|---|---|---|---|
| No fortification | O.D. | 0.0 | 0.04 | 0.0 |
|  | pH | 7.1 | 6.9 | 6.9 |
| Yeast Extract (8.00 g/l) | O.D. | 0.0 | 0.06 | 0.07 |
|  | pH | 6.8 | 6.5 | 6.5 |
| Cottage Cheese Whey (3.44 g/l) | O.D. | 0.05 | 0.54 | 0.66 |
|  | pH | 6.4 | 4.7 | 4.3 |
| Yeast Extract and Cottage Cheese Whey | O.D. | 0.02 | 0.56 | 0.83 |
|  | pH | 6.3 | 4.6 | 4.3 |

TABLE 4

Growth of L. acidophilus in a medium composed of collagen (16 g/l) and starch (2 g/l) which has been modified by the addition of yeast and cheese whey

|  |  | 4 hr | 12 hr | 24 hr |
|---|---|---|---|---|
| No fortification | O.D. | 0.0 | 0.0 | 0.0 |
|  | pH | 6.6 | 6.6 | 6.6 |
| Yeast Extract (8.00 g/l) | O.D. | 0.0 | 0.0 | 0.02 |
|  | pH | 6.4 | 6.2 | 6.2 |
| Cottage Cheese Whey (3.44 g/l) | O.D. | 0.04 | 0.87 | 0.94 |
|  | pH | 5.8 | 4.6 | 4.1 |
| Yeast Extract and Cottage Cheese Whey | O.D. | 0.03 | 0.90 | 1.02 |
|  | pH | 5.8 | 4.4 | 4.2 |

TABLE 5

Results of response surface experiment[2]

| Trial Number | Collagen concentration (grams/liter) | Starch concentration (grams/liter) | Bacillus subtilis growth (O.D.) | Reducing sugar production (grams/liter) | Lactobacillus acidophilus growth in fortified (3.14 g/l cheese whey) media (O.D.) | Lactobacillus acidophilus growth in unfortified media (O.D.) |
|---|---|---|---|---|---|---|
| 31 | 20 | 2 | 0.16 | 0.50 | 0.25 | — |
| 32 | 80 | 2 | 0.30 | 1.19 | 0.32 | 0.08 |
| 33 | 20 | 10 | 0.22 | 0.54 | 0.21 | 0.01 |
| 34 | 80 | 10 | 0.35 | 1.69 | 0.40 | 0.10 |
| 35 | 20 | 6 | 0.19 | 0.55 | 0.30 | 0.05 |
| 36 | 80 | 6 | 0.36 | 1.39 | 0.37 | 0.11 |
| 37 | 50 | 2 | 0.40 | 1.01 | 0.27 | 0.04 |
| 38 | 50 | 10 | 0.35 | 1.13 | 0.52 | 0.09 |
| 39 | 50 | 6 | 0.39 | 1.23 | 0.45 | 0.11 |
| 40 | 50 | 6 | 0.34 | 1.12 | 0.42 | 0.10 |
| 41 | 50 | 6 | 0.41 | 1.13 | 0.42 | 0.10 |

TABLE 6

Effect of different fortifying materials on Lactobacillus acidophilus growth in medium composed of 16 g/l collagen and 2 g/l starch modified by Bacillus subtilis growth (4 hrs)

|  | 3.14 g/l Cheese Whey | 1.00 g/l Glucose | No Additive |
|---|---|---|---|
| Growth of L. acidophilus (O.D.) | 0.26 | 0.22 | 0.13 |

TABLE 7

Growth of Bacillus sp. (O.D.) in medium composed of 50 g/l collagen and 10 g/l starch

| Time (hrs) | Bacillus megaterium | Bacillus natto | Bacillus polymyxa |
|---|---|---|---|
| 2 | 0.02 | 0.02 | 0.015 |
| 4 | 0.18 | 0.14 | 0.06 |
| 6 | 0.58 | 0.52 | 0.23 |
| 23 | 4.80 | 3.90 | 1.38 |

Figure 6:
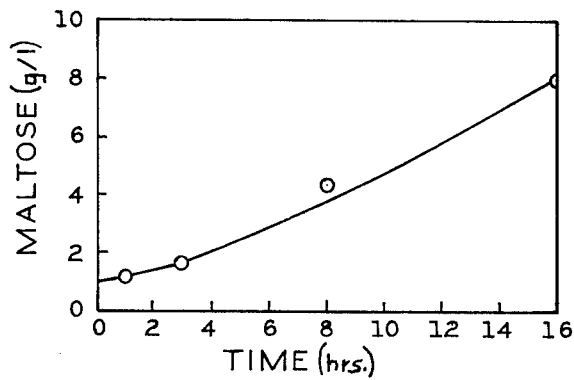
FIG. 6 is a graph showing the effect of extended incubation following lysis of B. subtilis on reducing sugar concentration.

An experiment to test the effect of extended incubation following lysis of B. subtilis cells grown for 4 hours in optimum medium (50 g/l collagen and 10 g/l starch) on reducing sugar concentration and subsequent L. acidophilus growth was performed (FIG. 6).

As expected, reducing sugar concentration increased until a limit of approximately 8 g/l was obtained and the starch in the medium had disappeared. After this point, reducing sugar concentration decreased, possibly as a result of the growth of contaminating microorganisms. An increase in L. acidophilus growth after increased incubation times was also noted.

Further experiments have demonstrated that Bacillus megaterium, B. natto and B. polymyxa all give adequate growth in optimum medium (Table 7). B. megaterium gives luxuriant growth as well as the most significant amylase production as measured on a nutrient agar plate containing 2% starch and tested with 1% $I_2$-KI solution. Likewise, Lactobacillus lactis and Lactobacillus casei both give adequate growth in modified optimum medium (Table 8).

The invention is further illustrated by the following: Ground beef from chuck roast (216 g) and grated whole potato (92 g) were mixed with 250 cc distilled $H_2O$. The mixture was steamed for about 1 hour. This process gave a slurry which was filtered to give a clear yellow colored solution. This solution was diluted to 500 ml. Screw top Erlenmeyer flasks (125 ml) were filled to 25 ml with this solution. Bacillus subtilis cells were inoculated into three flasks and grown for a period of time in excess of 24 hours. The final O.D. was in excess of 1.1.

TABLE 8

Growth of Lactobacillus sp. in medium initially containing 50 g/l collagen and 10 g/l starch modified by Bacillus subtilus growth (4 hrs)

|  |  | Lactobacillus acidophilus | Lactobacillus casei | Lactobacillus lactis |
|---|---|---|---|---|
| No fortification | O.D. | 0.10 | 0.04 | 0.04 |
|  | pH | 6.2 | 6.3 | 6.6 |
| Cottage cheese whey (3.44 g/l) | O.D. | 0.38 | 0.32 | 0.23 |
|  | pH | 4.5 | 4.8 | 5.1 |

Although the invention is described in terms of batch processing, it is adaptable to continuous operation utilizing well known continuous fermentation techniques. In such a continuous process about 50% yield of the single cell protein product is taken out each 30 minutes to 1 hour. The average incubation time in such a system is about one hour.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A method of producing and recovering protein from food wastes, which method comprises:
   A. preparing a mixed liquid medium from a combination of protein-containing and carbohydrate-containing food wastes,
   B. inoculating said medium with a species of Bacillus,
   C. maintaining the medium under conditions favorable to microbial growth for a time sufficient to produce a Bacillus-modified enriched medium,
   D. inoculating the resulting modified medium with a species of Lactobacillus,
   E. maintaining the resulting medium under conditions favorable for microbial growth for a time sufficient to produce Lactobacillus in the enriched medium, and
   F. extracting and recovering the resulting Lactobacillus single cell protein 2. A method according to claim 1 further characterized in that said protein-containing food waste comprises collagen and said carbohydrate-containing food waste comprises starch.

3. A method according to claim 2 further characterized in that said food wastes are present in the medium in the proportion of about 5 to 200 grams collagen per liter of medium and about 1 to 20 grams starch per liter.

4. A method according to claim 1 further characterized in that said Bacillus inoculated medium is maintained between about 20° to 70° C for about 1 to 36 hours.

5. A method according to claim 1 further characterized in that said Lactobacillus inoculated modified medium is maintained between about 20° to 70° C for about 1 to 36 hours.

6. A method according to claim 1 further characterized in that Bacillus cells are lysed with lysozyme and the medium is incubated after lysis at between about 20° to 70° C.

7. A method according to claim 1 further characterized in that the Bacillus inoculated medium is fortified with a sugar containing material.

8. A method according to claim 7 further characterized in that said fortifying material is cheese whey added in amount equal to about 3.5 grams per liter.

9. A method according to claim 7 further characterized in that said medium is further fortified with brewer's yeast cells.

10. A method according to claim 1 further characterized in that:
  A. said mixed liquid medium comprises collagen in the proportion of about 5 to 200 grams per liter and starch in the proportion of about 1 to 20 grams per liter,
  B. said Bacillus-containing medium is maintained between about 20° and 70° C for about 1 to 36 hours, and
  C. said modified Lactobacillus-containing medium is maintained between about 20° to 70° C for about 1 to 36 hours.

11. A method according to claim 10 further characterized in that the Bacillus inoculated medium is fortified with a sugar containing material.

12. A method according to claim 11 further characterized in that said fortifying material is cheese whey added in amount equal to about 3.5 grams per liter.

13. A method according to claim 11 further characterized in that said medium is further fortified with brewer's yeast cells.

* * * * *

UNITED STATES PATENT AND TRADEMARK OFFICE
CERTIFICATE OF CORRECTION

PATENT NO. : 4,018,650
DATED : April 19, 1977
INVENTOR(S) : Francis F. Busta et al It is certified that error appears in the above-identified patent and that said Letters Patent are hereby corrected as shown below:

Column 1, line 67, "7.2." should be --7.12.--.

Column 4, line 61, after "protein", insert --by--.

Signed and Sealed this

Twenty-first Day of June 1977

[SEAL]

Attest:

RUTH C. MASON
Attesting Officer

C. MARSHALL DANN
Commissioner of Patents and Trademarks